(12) United States Patent
Tolosa et al.

(10) Patent No.: US 9,560,974 B2
(45) Date of Patent: Feb. 7, 2017

(54) LUMINESCENCE BASED NONINVASIVE REMOTE PARAMETER SENSOR AND SENSING METHOD

(75) Inventors: Leah Tolosa, Crownsville, MD (US);
Hung Lam, Baltimore, MD (US);
Yordan Kostov, Columbia, MD (US);
Steven M Falk, Baltimore, MD (US);
Govind Rao, Ellicott City, MD (US)

(73) Assignee: University of Maryland Baltimore County, Baltimore, MD (US)

(*) Notice: Subject to any disclaimer, the term of this patent is extended or adjusted under 35 U.S.C. 154(b) by 233 days.

(21) Appl. No.: 13/539,067

(22) Filed: Jun. 29, 2012

(65) Prior Publication Data

US 2013/0079661 A1    Mar. 28, 2013

Related U.S. Application Data

(63) Continuation-in-part of application No. 13/501,081, filed on Jul. 23, 2012, now abandoned.

(60) Provisional application No. 61/502,542, filed on Jun. 29, 2011.

(51) Int. Cl.
*A61B 5/00* (2006.01)
*A61B 5/01* (2006.01)

(52) U.S. Cl.
CPC ............ *A61B 5/01* (2013.01); *A61B 5/0071* (2013.01); *A61B 5/6832* (2013.01); *A61B 5/74* (2013.01); *A61B 2503/045* (2013.01)

(58) Field of Classification Search
CPC .......... A61B 5/01; A61B 5/015; G01K 13/002
USPC ........................................................ 600/549
See application file for complete search history.

(56) References Cited

U.S. PATENT DOCUMENTS

| | | | |
|---|---|---|---|
| 4,323,077 A * | 4/1982 | Smith | ............................. 600/437 |
| 4,874,492 A | 10/1989 | Mackay | |
| 5,580,527 A | 12/1996 | Bell et al. | |
| 5,708,957 A | 1/1998 | Chuang et al. | |
| 6,123,455 A | 9/2000 | Beshears et al. | |
| 6,285,807 B1 | 9/2001 | Walt et al. | |
| 6,847,913 B2 | 1/2005 | Wigley et al. | |
| 8,005,624 B1 * | 8/2011 | Starr | ................................ 702/19 |

(Continued)

FOREIGN PATENT DOCUMENTS

EP    1 525 842 A1    4/2005
WO    WO9318745 A1 *  9/1993

OTHER PUBLICATIONS

Buttgen, B. et al., "CCD/CMOS Lock-In Pixel for Range Imaging: Challenges, Limitations and State-of-the-Art," Paper presented in the Proceedings of the First Range Imaging Research Day (pp. 21-32), Zurich, Switzerland, 2005.*

(Continued)

*Primary Examiner* — Daniel Cerioni
(74) *Attorney, Agent, or Firm* — Rene A. Vazquez, Esq.

(57) ABSTRACT

A noninvasive remote parameter sensor and sensing method is provided that is particularly suited for the remote monitoring of skin temperature. The sensor and sensing method utilize luminescence-based sensors that are non-toxic and non-irritating to the skin. The sensor preferably utilizes one or more types of fluorophores that are embedded in a soft hydrogel. The sensor is illuminated with excitation light, and temperature is monitored by detecting and analyzing the emission light from the fluorophores. Because a soft hydrogel is used, the sensor can be gently wiped off the skin at the conclusion of temperature measurements.

18 Claims, 10 Drawing Sheets

(56) References Cited

U.S. PATENT DOCUMENTS

| | | | |
|---|---|---|---|
| 2003/0050543 A1 | 3/2003 | Hartmann | |
| 2005/0112151 A1* | 5/2005 | Horng | 424/401 |
| 2005/0148003 A1 | 7/2005 | Keith et al. | |
| 2005/0267382 A1 | 12/2005 | Church et al. | |
| 2007/0128681 A1 | 6/2007 | Barman et al. | |
| 2007/0166780 A1 | 7/2007 | Wilson | |
| 2008/0131512 A1 | 6/2008 | Hennink et al. | |
| 2009/0130773 A1 | 5/2009 | Ayi et al. | |
| 2010/0063371 A1 | 3/2010 | Müller et al. | |
| 2011/0048946 A1* | 3/2011 | Desai et al. | 204/451 |
| 2012/0330126 A1* | 12/2012 | Hoppe et al. | 600/391 |

OTHER PUBLICATIONS

Beleizao, "Dual Fluorescence Sensor for Trace Oxygen and Temperature with Unmatched Range and Sensitivity", Anal. Chem., vol. 80, No. 26, Aug. 2008, pp. 6449-6457.

Someya et al., "Combined measurement of velocity and temperature distributions in oil based on the luminescent lifetimes of seeded particles; Combined measurement of velocity and temperature distributions in oil", Measurement Science and Technology, vol. 20, No. 2, Feb. 2009, p. 25403.

Gramlich et al., "Diffusion of [alpha]-Tocopherol in Membrane Models: Probing the Kinetics of Vitamin E Antioxidant Action by Fluorescence in Real Time", Journal of the American Chemical Society, vol. 126, No. 17, May 2004, pp. 5482-5492.

Orcel et al., "Effect of formamide additive on the chemistry silica sol-gels II. Gel structure", Journal of Non-Crystalline Solids, vol. 105, No. 3, Nov. 1988, pp. 223-231.

Yap et al., Temperature dependent characteristics of La2O2S: Ln[Ln 1/4 Eu, Tb] with various Ln concentrations over 5-60C, Journal of Luminescence 129 (2009; Available online Nov. 27, 2008), 416-422.

Lochmann et al., Luminescence lifetime determination for oxygen imaging in human tissue, Laser Phys. Lett. 5, No. 2, 151-155 (2008) / DOI 10.1002/lapl.200710096.

* cited by examiner

LUMINESCENCE BASED NONINVASIVE REMOTE PARAMETER SENSOR AND SENSING METHOD

This application is a continuation-in-part of U.S. patent application Ser. No. 13/501,081, filed Apr. 9, 2012. This application also claims priority to U.S. Provisional Application Ser. No. 61/502,542, filed Jun. 29, 2011, whose entire disclosure is incorporated herein by reference.

BACKGROUND OF THE INVENTION

1. Field of the Invention

The present invention relates to the noninvasive, remote sensing of predetermined parameters such as, for example, remote sensing of human body temperature.

2. Background of the Related Art

Internal body temperature is a physiologic variable that is precisely controlled by the body. Chemical processes and enzymes required to catalyze the associated chemical reactions, thereby regulating cellular function, optimally operate within this narrow thermal bandwidth. Thermoregulation encompasses all physiological processes and responses that balance heat production and heat loss to maintain body temperature within this normal range. Compared to the adult or older pediatric model, thermoregulation is even more critical to neonatal care.

Compared to adults, newborns are particularly vulnerable to temperature extremes. If heat loss is not preempted, newborns could suffer the ill effects of cold stress or hypothermia. Depending on the gestational age, mortality may increase by 10% for each degree Celsius (° C.) that a baby's body temperature is below 36° C. Conversely, at relatively high temperatures, infants may be subjected to the dangers of heat stress or hyperthermia. Both types of thermal stresses, hypo- and hyperthermia can be a significant cause of morbidity and mortality in this vulnerable population. Thus, in the hospital setting, infant incubators are designed to keep the infant in an environment of constant temperature.

Nonetheless, providing optimal thermal conditions to the newborn require the body temperature to be measured. To date, wired thermistors are conventionally employed that are attached to a neonate's skin using a strong adhesive to keep them in place. However, adhesive use on the thermistor probe cover is not an innocuous intervention. Investigations have shown increased microbial growth beneath probe covers, some of which have proved to be pathogenic. Others have found skin impairment ranging from chemical sensitivities to prolonged mechanical force on the skin from some adhesives. Adhesives can irritate the skin by occlusion or by altering the skin morphology via epidermal stripping. The removal of adhesively-attached skin temperature probes can result in "skin tears" in which shear or frictional forces separate the dermis from the epidermis.

These tears can compromise skin barrier function, cause a marked increase in transepidermal water loss and, in many cases, disrupt the skin's ability to protect against microorganism invasion. Especially for extremely premature neonates, the adhesive poses a high potential risk of injury due to their immature skin. Studies have shown that at 24 weeks gestation, premature neonates have little stratum corneum and attenuated rete ridges. Their skin is red, wrinkled, translucent, and gelatinous in appearance. They lack subcutaneous tissue, therefore, their dermis is lying directly over the muscle. Consequently, skin stripping secondary to adhesive dressing and/or tape removals can result in full-thickness tissue loss.

Even at 36 weeks (full term), the epidermal and dermal layers of neonates, although structurally similar to an adult, are just up to 60% as thick as those in an adult. As a result, epidermal stripping secondary to tape and adhesive dressing removal is most common in neonates born before 27 weeks gestation and is the primary cause of skin breakdown in the Neonatal Intensive Care Unit (NICU). Given the neonate's attenuated rete ridges, adhesive products typically bond more aggressively to the epidermis than the epidermis does to the dermis. Consequently, epidermal stripping is not only a source of discomfort, but can also lead to other morbidity in very low birth weight neonates and those who are immune-compromised.

Skin friendly adhesives that can hold the wired probe in place while minimizing trauma to the skin have not yet been developed. Alternative temperature probes that can eliminate adhesives also are nonexistent. In addition, remote thermal-imaging systems that may offer non-adhesive, non-contact features and a resolution of 0.3° C. are still too expensive for general use in the NICU.

SUMMARY OF THE INVENTION

An object of the invention is to solve at least the above problems and/or disadvantages and to provide at least the advantages described hereinafter.

Therefore, an object of the present invention is to provide a system and method for the remote sensing of a parameter, such as temperature, in a non-invasive and/or non-contact manner.

Therefore, an object of the present invention is to provide a system and method for the remote sensing of a parameter, such as temperature, in a non-invasive and/or non-contact manner.

Another object of the present invention is to provide a system and method for remotely measuring body temperature in a non-invasive and/or non-contact manner.

Another object of the present invention is to provide a system and method for remotely measuring the body temperature of an infant in a non-invasive and/or non-contact manner.

Another object of the invention is to provide a luminescence-based temperature sensor and sensing method;

Another object of the invention is to provide a luminescence-based gel sensor that can be gently applied to and removed from human skin;

To achieve at least the above objects, in whole or in part, there is provided a noninvasive remote sensor for measuring a parameter of a system, comprising a gel, and a first type of fluorophore embedded in the gel, wherein the first type of fluorophore emits first emission light in response to excitation light, and wherein a chemical property of the type of fluorophores is such that at least one characteristic of the first emission light varies as a function of changes in the parameter being measured.

To achieve at least the above objects, in whole or in part, there is also provided a sensor for remotely monitoring the temperature of an object, comprising a gel adapted to be applied to the object, and a first type of fluorophore embedded in the gel, wherein the first type of fluorophore emits first emission light in response to excitation light, and wherein a chemical property of the first type of fluorophore is such that at least one characteristic of the first emission light varies as a function of temperature.

To achieve at least the above objects, in whole or in part, there is also provided a method of monitoring skin temperature, comprising applying a luminescence-based gel sensor to skin, wherein the luminescence-based gel sensor comprises a first type of fluorophore embedded in a gel, illuminating the luminescence-based gel sensor with excitation light, detecting emission light from the first type of fluorophore, and determining the skin temperature based on the detected emission light.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
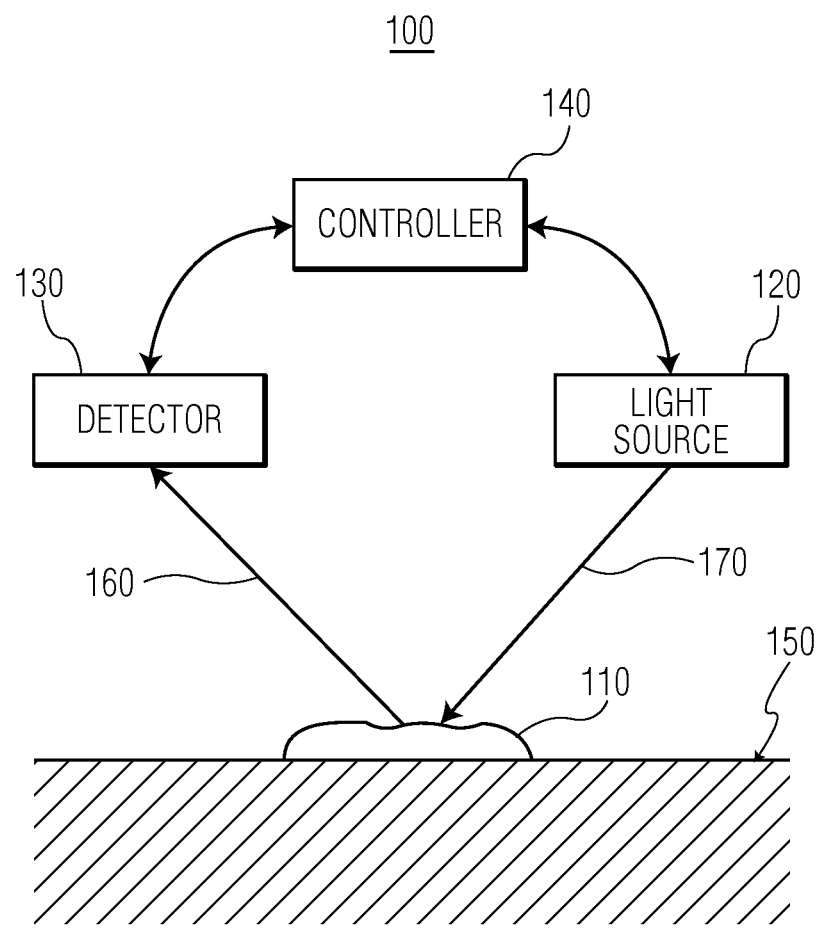
FIG. 1 is a schematic diagram of a noninvasive remote parameter sensing system that utilizes a luminescence-based sensor, in accordance with one embodiment the present invention.

By way of example, the present invention will be described in connection with a noninvasive remote temperature sensor and sensing method that is particularly suited for the remote sensing of skin temperature in infants. However, it should be appreciated that the present invention can be used as a remote sensor for other types of parameters such as, for example, $CO_2$, pH, ammonia, oxygen, sodium, calcium and potassium.

Throughout the specification, the terms luminophore and fluorophore are used interchangeably and both refer to a chemical compound that re-emits light upon light excitation.

The present invention utilizes luminescence-based sensing. In a preferred embodiment for temperature sensing, a temperature sensing luminophore is incorporated in a soft hydrogel that can then be applied gently on human skin. The adhesion on the skin is strong enough that it does not fall off, but can also be gently wiped off at the conclusion of temperature measurements.

A variety of luminophores have been found to show high sensitivity to temperature. The luminescence intensities and decay times of these compounds decrease with increasing temperatures and can be measured with a high degree of accuracy. Thus, many luminophores have been previously utilized as luminescent temperature probes. However, most of these are not suitable for healthcare applications, particularly neonatal healthcare applications. As an example, alexandrite crystals have been found to be sensitive between 15°-45° C., and the phosphorescence decay time decreases from 300 to 220 microseconds within this range. The long decay time is easy to precisely measure with low cost instrumentation. While these properties may seem appropriate for healthcare applications, alexandrite crystals cannot be ground to a fine powder for application on human skin. Additionally, the grinding process creates defects on the crystal structure which render alexandrite non-luminescent.

Many other materials, such as zinc sulfide and lanthanide phosphors (e.g., $La_2O_2S:Eu$) also show strong temperature sensitivity over the desired range of temperatures. The lanthanide phosphors also show desirable lifetime changes as the temperature changes. Unfortunately, all of these luminophores are only excitable by UV light, which is potentially harmful to human skin, particularly neonatal skin.

In contrast to UV-excited materials, there are classes of luminophores that are excitable by visible light, such as ruthenium(II) tris(1, 10-phenanthroline) (Ruphen) and ruthenium(II) tris(bipyridine) (Rubpy). These dyes are not only highly luminescent, but their luminescence intensity and decay times are also very sensitive to temperature. Moreover, they have been found to be nontoxic and incapable of penetrating human skin.

These dyes that are excitable with visible light have been widely employed as temperature probes in various research fields. Luminescence-based temperature probes have a variety of advantages over thermoelectric probes, including immunity to high electromagnetic fields, the suitability for long distance measurements, and virtually unlimited spatial resolution. For instance, luminophores can be employed in thermal convection studies in both huge bioreactors and micro-sized lab-on-a-chip environments. Furthermore, since light transmission requires no conducting medium, the probe and the photodetector need not to be in direct contact. Accordingly, remote detection can be realized. Due to the advantages of luminescence sensors, a number of luminescence-based temperature probes have been developed.

FIG. 1 is a schematic diagram of a noninvasive remote parameter sensing system 100 that utilizes a luminescence-based sensor 110, in accordance with one embodiment of the present invention. The remote parameter sensing system 100 includes a luminescence-based sensor 110, a light source 120, a detector 130 and a controller 140. The luminescence-based sensor 110 is in contact with a surface 150 where the parameter, such as temperature, is to be measured, and is preferably a gel that is embedded with a chemical that emits light 160, via luminescence, when it is excited by excitation light 170 from the light source 120 at an appropriate excitation frequency. The chemical properties of the luminescence-based sensor 110 are such that at least one characteristic of the emission light 160 (such as, for example, emission intensity) varies as a function of variations in the parameter being measured.

The controller 140 controls the measurement process, including control of the light source 120, receiving detector signals from the detector 130 and processing and analyzing the detector signals to analyze the parameter being measured.

Figure 2:
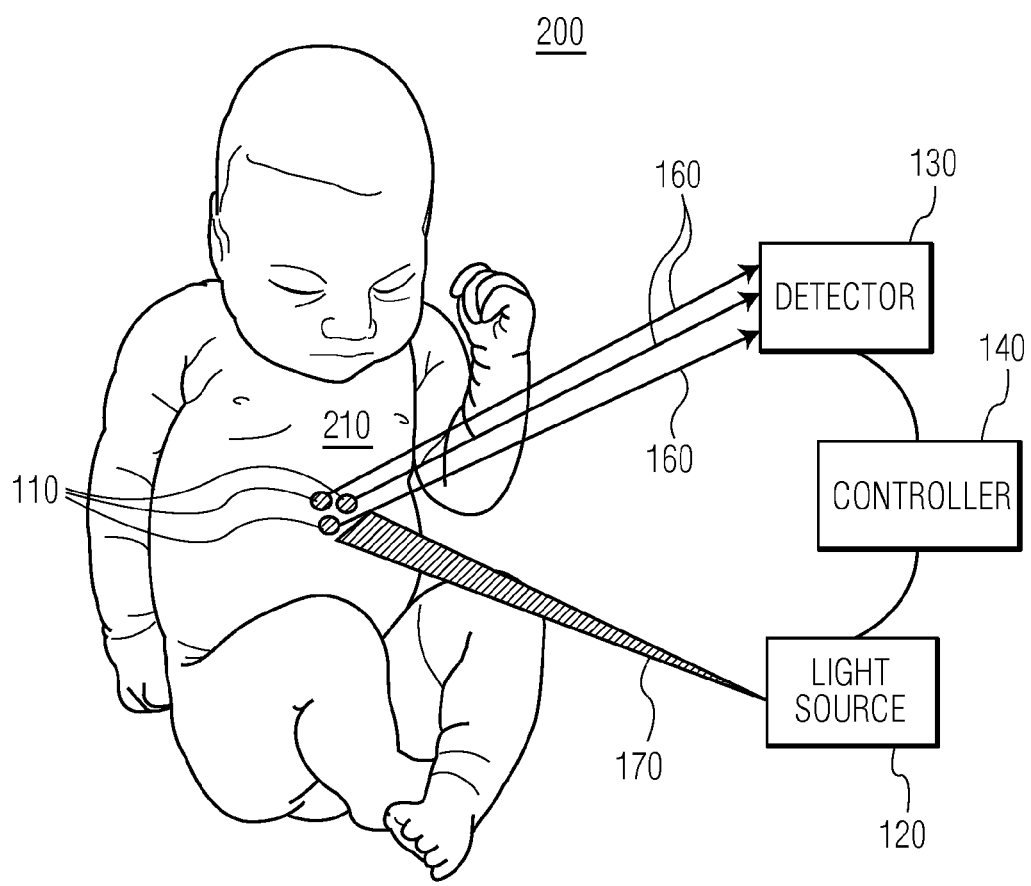
FIG. 2 is a system for remotely monitoring body temperature that utilizes a luminescence-based gel sensor, in accordance with one embodiment the present invention.

FIG. 2 is a schematic diagram of a system 200 for remotely and noninvasively monitoring body temperature utilizing one or more luminescence-based gel sensors 110, in accordance with another embodiment of the present invention. The system 200 includes a light source 120, detector 130, controller 140, and at least one luminescence-based gel sensor 110 placed on the skin 210 of the subject whose temperature is being measured.

The luminescence-based gel sensors 110 are preferably applied onto multiple sites on the subject's skin 210. The luminescence-based gel sensors are illuminated from a distance with excitation light 170 from light source 120, and the emission light 160 is detected by detector 130. The detector signals are then analyzed by controller 140. In one preferred embodiment, the detector 130 is a movable CCD camera and the controller 140 is programmed with shape recognition software for controlling the position of the CCD camera to follow the luminescence-based gel sensors 110 as the subject moves.

The temperature sensing system 200 offers many advantages of over existing systems. First, there is no need for problematic adhesives to keep the luminescence-based gel sensors 110 in place. It is very easy to daub the luminescence-based gel sensors 110 on the skin 210, and the luminescence-based gel sensors 110 can be removed easily by gentle wiping with a wet tissue. Thus, the skin 210 will not be exposed to any stress associated with applying and removing an adhered probe.

Another advantage is the flexibility of the luminescence-based gel sensors 110. For example, luminescence-based gel sensors 110 can be smeared anywhere and at multiple points on the subject. In contrast, taking temperature readings at multiple points with wired thermistors can be very cumbersome, and creates the added danger of an infant getting caught in a tangle of wires. Further, as the luminescence-based gel sensors 110 are always in close contact with the skin 210, optimal heat transfer from the skin 210 to the luminescence-based gel sensors 110 are ensured at all times, thereby increasing the accuracy of the temperature measurement and its correlation to core body temperature.

While temperature sensing luminophores have been used in the art, they require UV light excitation, which is not acceptable for humans (particularly infants), or they emit light in the IR wavelength range where radiant warmers will interfere. The luminescence-based gel sensors 110 in system 200 are preferably designed to be excited with and emit light in the visible wavelength range.

As discussed above, the luminescence-based gel sensors 110 are preferably temperature sensitive nontoxic luminophores in a hydrogel matrix. The preferred properties of the luminophores and hydrogel matrix will now be discussed.

In general, there are three approaches for measuring temperature: (1) steady state luminescence intensity measurements; (2) ratiometric intensity measurements; and (3) decay time measurements. The simplest is approach (1), which measures the steady state luminescence intensity. However, this approach is not suitable for long term measurements, as the intensity can drift due to photobleaching of the luminophore. Methods (2) and (3) offer solutions to this problem.

Approach (2) takes the intensity ratio of two emission bands of the luminophore system to represent the temperature. Assuming the photobleaching effect has the same impact on the emission bands, the ratio is unaffected, thereby making the system less prone to drift.

Approach (3) utilizes the decay time of the luminophore as the temperature sensitive parameter. The decay time is the time span required for the luminophore dye at the excited state to return to the electronic ground state. This transition is temperature dependent. Since it is an intrinsic property of the dye molecule, the temperature measurement based on the decay time technique is entirely independent of the luminophore concentration.

The luminescence process is initiated by the absorption of light by the ground state luminophore, and in the process promoting the molecule to an electronic excited state. The ruthenium luminophores mentioned above (Ruphen and Rubpy) undergo intersystem crossing from the lowest singlet excited state to the triplet state (technically a singlet-triplet hybrid), which is normally at a lower energy. Return of the triplet to the singlet ground state requires intersystem crossing, i.e. a "forbidden" process. This explains both the long decay lifetimes, as well as the red-shifted emission.

In a preferred embodiment, the luminescence-based gel sensor 110 is made up of two different types of fluorophores in a hydrogel matrix. The two fluorophores are preferably Ruphen and 8-aminopyrene-1,3,6-trisulfonic acid ("APTS").

The fluorophores Ruphen and APTS are an ideal fluorophore pair for ratiometric temperature measurement. In Ruphen, the ruthenium ion Ru(II) forms an octahedral complex with three phenanthroline molecules. The complex has a strong absorption band at around 450 nm due to the very prominent metal to ligand charge transfer transition (MLCT) to the triplet MLCT state that is energetically slightly lower than the triplet d-d state. The transition from the MLCT state to the ground state results in emission of light (at 590 nm) whereas the promotion to the d-d state by thermal energy leads to the radiationless decay to the ground state. These two processes compete at any given temperature. Hence, less fluorescence emission is observed at higher temperatures and vice versa.

Figure 3A:
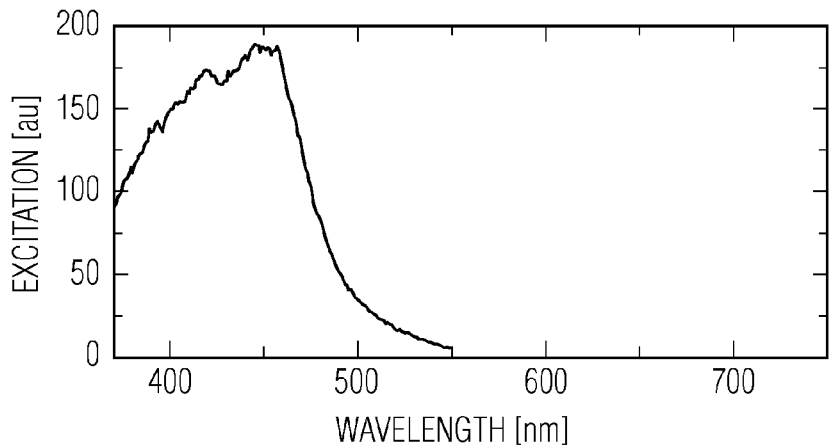
FIG. 3A is a plot of the excitation spectrum of Ruphen.

APTS, on the other hand, is a polycyclic aromatic compound consisting of 4 fused benzene rings. The excitation maximum is at around 420 nm in aqueous solution, whereas the emission peak is located at 500 nm. As shown on FIGS. 3A and 3D, both dyes can be excited by visible blue light, which is harmless to human skin and, therefore, acceptable for use on humans. Additionally, an inexpensive but efficient LED can be employed as a single excitation light source 120.

Figure 3B:
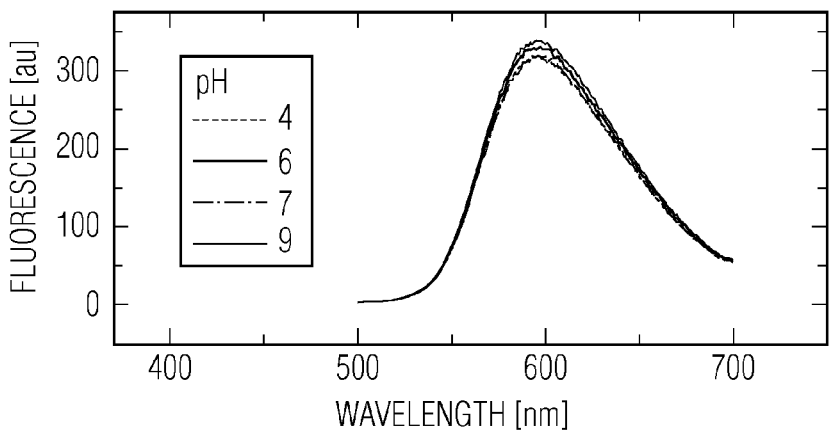
FIG. 3B is a plot of the emission spectrum of Ruphen at different pH values.
Figure 3C:
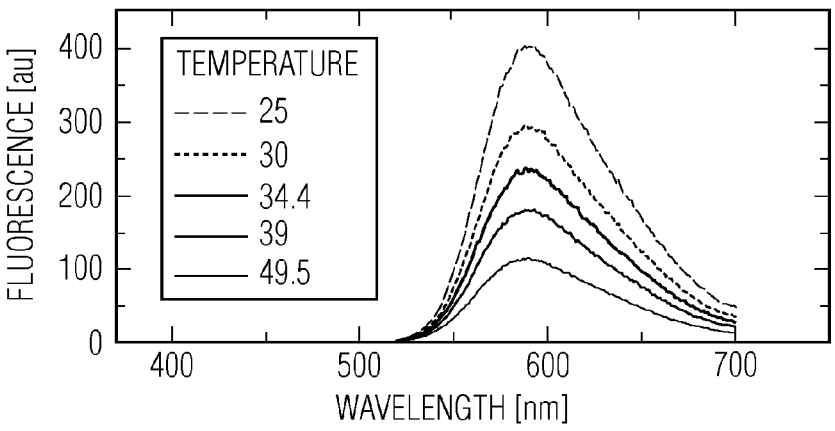
FIG. 3C is a plot of the emission spectrum of Ruphen at different temperatures.
Figure 3D:
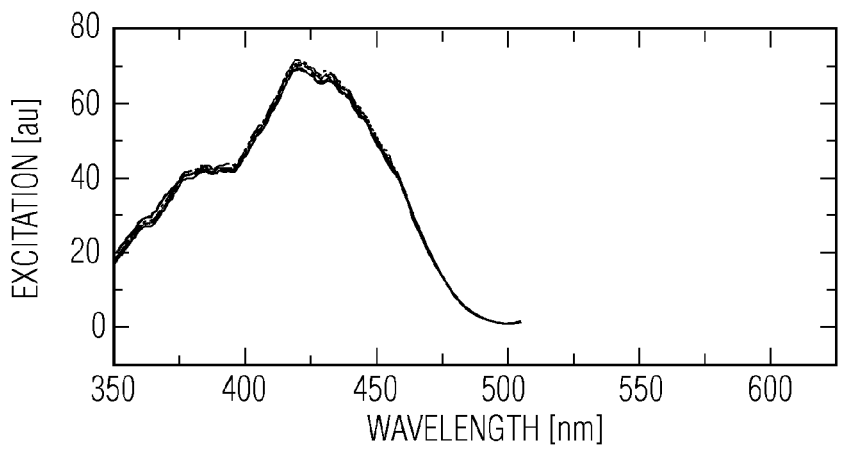
FIG. 3D is a plot of the excitation spectrum of APTS.
Figure 3E:
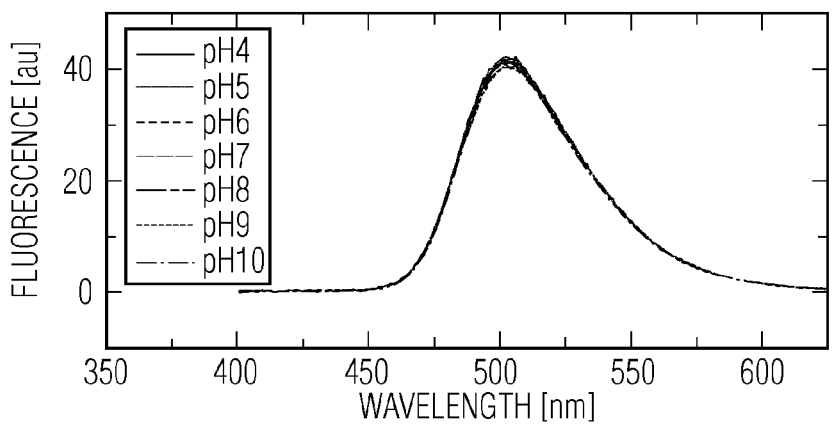
FIG. 3E is a plot of the emission spectrum of APTS at different pH values.

The emission peaks of Ruphen (FIGS. 3B and 3C) and APTS (FIGS. 3E and 3F) are about 90 nm apart. Accordingly, they can be easily isolated with the appropriate filters. Moreover, the fluorescence of Ruphen and APTS are only slightly affected by pH, as shown in FIGS. 3B and 3E, respectively. This is important, as the skin of neonates at different gestational ages have varying pH levels.

Figure 3F:
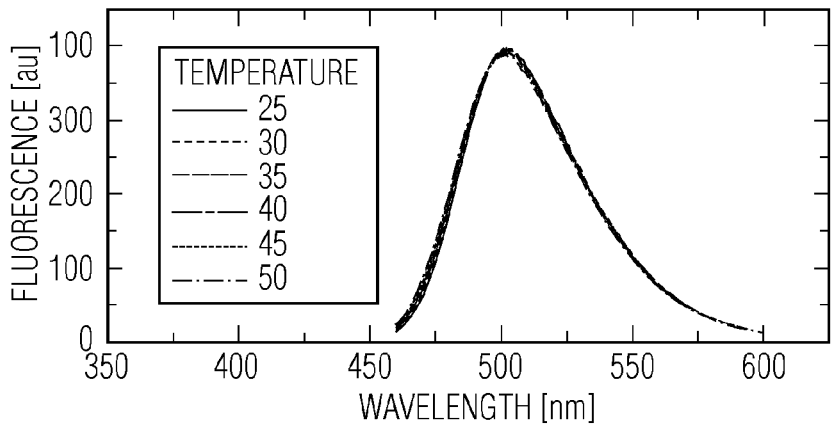
FIG. 3F is a plot of the emission spectrum of APTS at different temperatures.

More importantly, ambient temperature has varying impacts on the fluorescence of the two dyes. On the one hand, as shown in FIG. 3C, the fluorescence intensity of Ruphen drops drastically by 75 percent when the ambient temperature is changed from 25° C. to 50° C. The significant temperature sensitivity in the physiological range makes Ruphen an ideal body temperature sensor. On the other hand, the same temperature change has virtually no impact on the fluorescence of APTS, as shown in FIG. 3F. Thus, APTS makes a very good reference sensor for Ruphen in ratiometric temperature measurements.

As discussed above, there is a need for remote and non-adhesive temperature sensing for infants. To this end, the luminescence-based gel sensor 110 preferably utilizes a skin-friendly vehicle or matrix for the luminophore dyes. The matrix in which the sensing luminophores are incorporated is a replacement for the harmful adhesive currently used to keep thermistors in place.

The matrix provides several important functions. It is the affixing component that enables contact of the luminophore dyes with the skin 210. It encapsulates the dyes within a semi-solid structure preventing the dyes from being blown off (if powder) or wiped off (if liquid) from the skin 210. The matrix also provides good heat transfer from the skin/body to the temperature sensing luminophore dyes, allowing for precise body temperature measurements to be carried out.

In order to be used as a temperature sensor on a human subject, the matrix should be biocompatible, should not harbor harmful microorganisms and should be non-irritating to the skin 210. Also, the matrix should not excessively absorb heat from the radiant warmer in the incubator or other sources, as this can cause a temperature reading higher than the skin temperature. Further, while the matrix should adhere well to the skin 210, it should be easily removable without irritating or harming the skin 210.

During the last two decades, significant advances have been made in the development of biocompatible and biodegradable materials for biomedical applications. In the biomedical field, the goal is to develop and characterize artificial materials for use in the human body to measure, restore, and improve physiologic function, and enhance survival and quality of life.

Typically, inorganic (metals, ceramics, and glasses) and polymeric (synthetic and natural) materials have been used for such items as artificial heart-valves, (polymeric or carbon-based) and synthetic blood-vessels. However, the preferred matrix for the luminophores are hydrogels.

Hydrogels are a network of polymer chains that are water-insoluble and are highly absorbent. They can contain over 99% water, which makes them highly flexible like natural tissue. Applications for hydrogels cover a wide range of fields. For example, polylactic acids are used as scaffolds in tissue engineering, 2-hydroxypropyl-methacrylate polymers (HPMA) has been widely employed in drug delivery systems, and polyacrylic acid is used as the super-absorbent in disposable diapers. In addition, contact lenses are made from silicone or polyacrylamide (15).

Of particular interest are hydrogels used for wound dressings, as they have the desired properties suitable for the sensitive skin of neonates. As such, they create or maintain a moist environment so that the skin 210 cannot dry out. They are well permeable to oxygen, so that the skin 210 underneath can breathe. In addition, these hydrogels protect wounds from the entry of microbes. Moreover, they adhere firmly even on the wounds, and can be gently removed without irritation.

Glyceryl polyacrylate (GPA) and chitosan are the subjects of active research as antibacterial wound dressing gels. Chitosan is a linear polysaccharide composed of randomly distributed β-(1-4)-linked D-glucosamine and N-acetyl-D-glucosamine produced commercially by de-acetylation of chitin, the structural element in the exoskeleton of crustaceans (crabs, shrimp, etc.) and cell walls of fungi. The amino group in chitosan has a pKa value of ~6.5, thus, chitosan is positively charged and soluble in acidic to neutral solution with a charge density dependent on pH and the deacetylation value. This makes chitosan and its derivatives a bio-adhesive which readily binds to negatively charged surfaces, such as mucosal membranes.

Chitosan and its derivatives are approved to be hypoallergenic and antibacterial. Its high tensile and bioadhesive strength are advantageous for forming a tacky sensing layer. Further, it can be gently dissolved by a slightly acidic solution at pH 6.0.

Glyceryl polyacrylate (GP) is a clathrate gel known for its high water retention ability. It does not dry even when exposed to ambient air or subjected to vacuum for 48 hours. This property is particularly useful for inactivating microbes by depriving them of water through osmotic effect. Studies show that by adding a certain amount of glycerol, the viscosity of the gel can be controlled. This results in a product that can adhere well on the skin 210 but that can also be easily peeled off.

For at least the reasons set forth above, chitosan gel is preferably used as the hydrogel matrix in the luminescence-based gel sensor 110. The chitosan gel is preferably prepared as follows. Chitosan (medium molecular weight, Sigma) is dissolved in 0.1 M acetic acid (Sigma) to make a 2% w/v gel. To each gram of this gel, 0.5 g glycerol is added. To prepare the gels containing the fluorophores, 0.1 g of silica gel adsorbed with either Ruphen or APTS is added to 1 gram of the chitosan. The luminescence-based gel sensor 110 preferably includes both a Ruphen containing gel and an APTS containing gel.

The present invention preferably uses ratiometric measurements to measure temperature using the luminescence-based gel sensor 110. The ratiometric method has the advantage that the imaging system, as well as the data acquisition and processing system, need not be very sophisticated and fast. However, two luminescence signatures need to be measured to arrive at the ratio.

Figure 4:
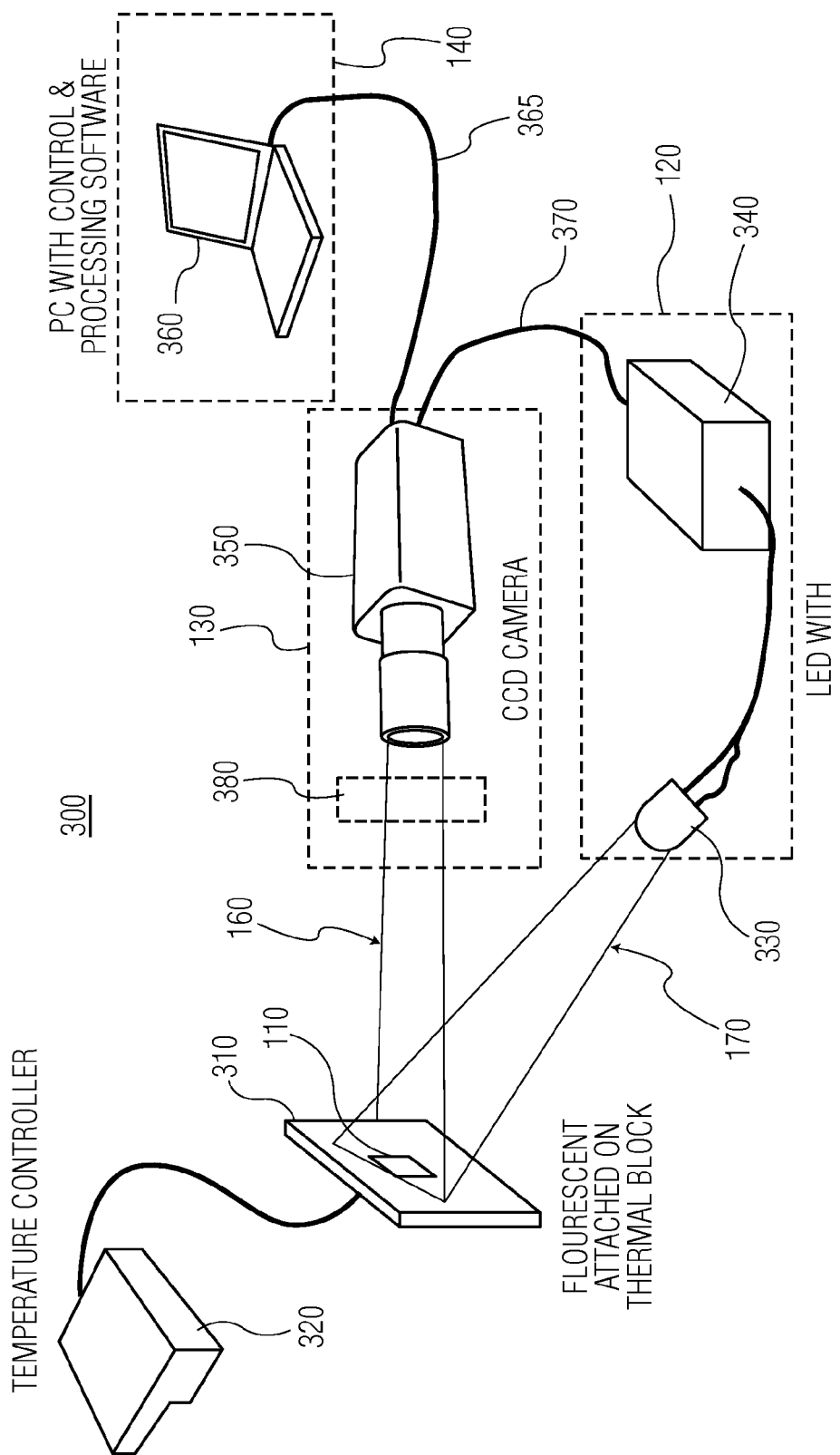
FIG. 4 is a schematic diagram of a system used to measure the effect of temperature on a luminescence-based gel sensor made up of a Ruphen containing hydrogel and an APTS containing hydrogel, in accordance with one embodiment of the present invention.

FIG. 4 is a schematic diagram of a system 300 used to measure the effect of temperature on a luminescence-based gel sensor 110 made up of a Ruphen containing hydrogel and an APTS containing hydrogel. The system 300 includes a thermal block 310 on which the luminescence-based gel sensor 110 is placed. A temperature controller 320 is used to control the temperature of the thermal block 310. A light source 120 that includes an LED 330 and an LED controller 340 is used to generate excitation light 170. A detector 130 that includes a CCD camera 350 is used to detect the emission light 160 from the luminescence-based gel sensor 110. For a luminescence-based gel sensor 110 made up of a Ruphen containing hydrogel and an APTS containing hydrogel, the LED is preferably a blue LED with an excitation peak at 475 nm.

The CCD camera 350 is controlled by controller 140. Controller 140 includes a computer 360 that is connected to the CCD camera 350 via cable 365. The CCD camera 350 transmits image data to and receives control commands from the computer 360. The CCD camera 350 is connected to the LED controller 340 via cable 370. The CCD camera 350 sends a timing signal to the LED controller 340 representing the time the CCD camera 350 makes an exposure. This timing signal is used to switch the LED 330 on and off.

If the Ruphen containing hydrogel and APTS containing hydrogel that make up the luminescence-based gel sensor 110 are mixed together or are otherwise not spatially separated from each other, then the emission light from the Ruphen and the emission light from the APTS will spatially overlap at the CCD camera 350. In this scenario, two different band pass filters must be used to isolate the Ruphen and APTS emission light. This can be suitably implemented incorporating a switchable band pass filter 380 in detector 130 that switches between a first band pass filter designed to pass the emission light from the Ruphen and a second band pass filter designed to pass the emission light from the APTS. The switchable filter 380 can be, for example, a filter wheel.

Another approach to discriminate between two spatially overlapping emission signals is a technique based on the decay time difference between two luminophores. When a luminophore is exposed to intensity modulated excitation light, the observed luminescence intensity is dependent on the modulation frequency $\omega$ and the luminophore decay time $\tau$. This dependency is described by the following equation: $f = s/(1+\omega^2 * \tau^2)^{-0.5}$, where s is the steady state luminescence intensity of the fluorophore, $\omega$ is the angular modulation frequency and $\tau$ is the decay time.

According to this equation, the modulated luminescence decreases with increasing modulation frequencies, eventually reaching a certain frequency where the luminescence is completely diminished (i.e., demodulated). The longer the decay time, the lower this boundary frequency is.

Suppose there are two luminophores in a system with a decay time difference of three orders of magnitude. When the system is excited with modulated excitation light at a frequency where the luminescence of the dye with longer decay time is demodulated, only the luminescence of the dye with shorter decay time will be observed.

At a lower frequency, emission from both the luminophores will be observed. Thus, one can calculate the ratio of the emission at the higher and lower excitation frequencies as an alternative to intensity ratios at two wavelengths. This technique has been successfully exploited for the determination of glucose and glutamine using fluorescently labeled periplasmic binding protein sensors.

Decay time measurements usually require sophisticated and fast performing imaging systems. Conventional methods use multi-channel plate (MCP) based image intensifiers. Unfortunately, MCPs are comparatively expensive, prone to photo-damage due to overexposure and require elaborate electronics. Moreover, MCP's spatial resolution is relatively low. Furthermore, MCPs can inject a comparatively high noise level in the measurement.

If the decay time technique is used, the controller 140 of system 300 preferably utilizes lock-in imaging for decay time measurements. This enables decay time measurements for a fraction of the cost and space of an MCP. The decay time can be determined by a phase modulation technique. In this approach, the luminescence modulated with a frequency $\omega$ is phase shifted in comparison to the excitation light. The phase shift $\phi$ is dependent on the decay time $\tau$ by the relation $\tau = \tan(\phi)/\omega$.

The phase shift can be determined with images from the CCD camera 350 as follows: Images are taken with phase delays (relative to the modulated excitation light) of 0, $0.5\pi$, $\pi$ and $1.5\pi$. The phase shift is calculated as $\phi = \arctan[(S_{1.5\pi} - S_{0.5\pi})/S0 - S_\pi)] - \phi'$, where $\phi'$ is the instrumental phase delay which can estimated by measuring the reflected excitation light. This technique is immune to interference from ambient light, which ensures precise temperature measurements.

If the Ruphen containing hydrogel and APTS containing hydrogel that make up the luminescence-based gel sensor 110 are positioned adjacent to each other or otherwise spatially separated from each other such their emission signals are spatially separated when they reach the CCD camera 350, and the CCD camera 350 can simultaneously image the emission light from both the Ruphen and APTS without the need for the switchable band pass filter 380. In this mode of operation, the LED 330 is switched on and off by the CCD camera 350 as follows.

Figure 5:
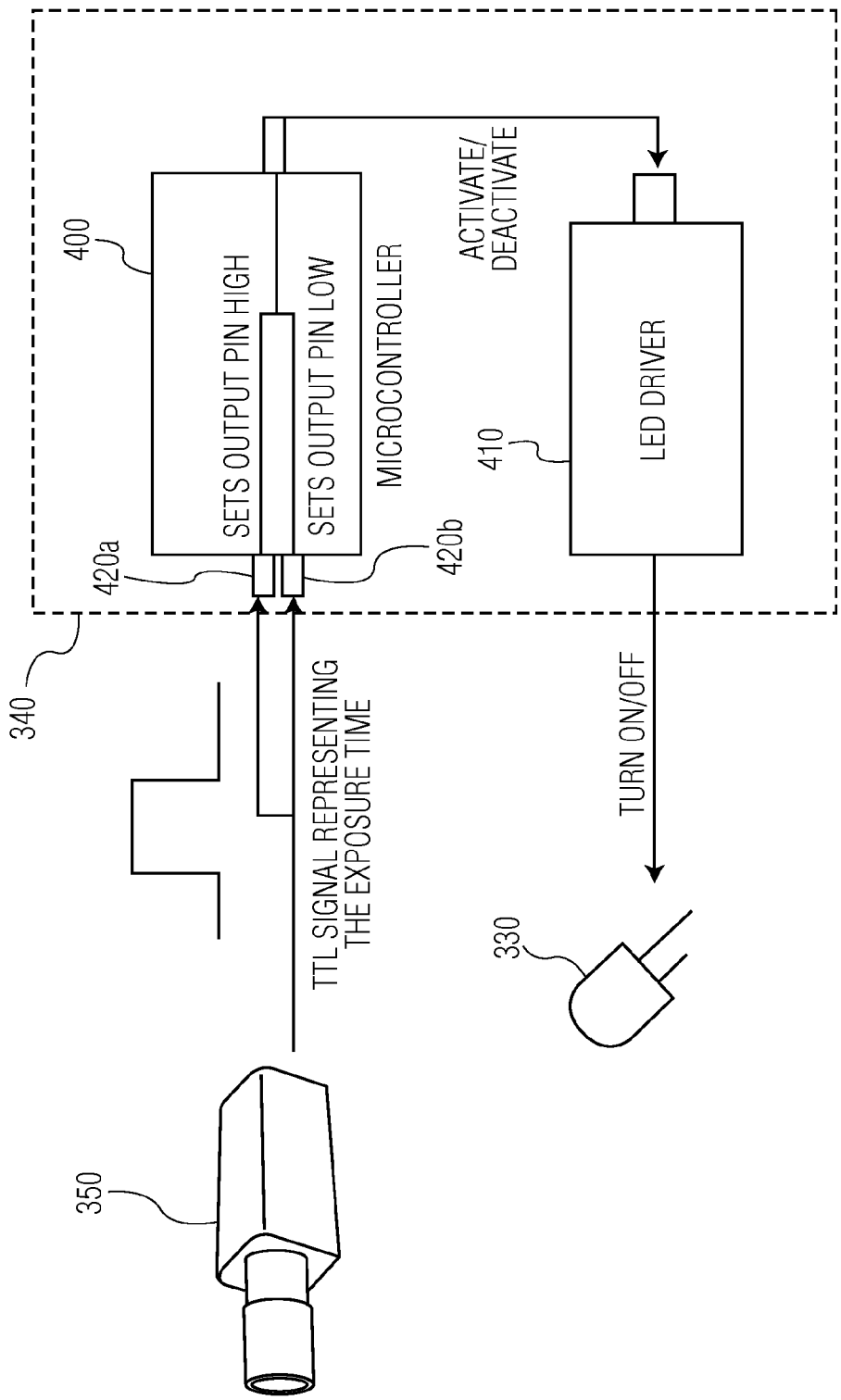
FIG. 5 is a schematic diagram of one preferred embodiment of the LED controller shown in FIG. 4.

As shown in FIG. 5, the LED controller 340 preferably includes a microcontroller 400 and an LED driver 410. The IO-port of the CCD camera 350 is connected to two external interrupt pins 410*a* and 420*b* on the microcontroller 400. The first interrupt responds to the rising edge of the camera output signal. The microcontroller 400 activates the current source by setting its PWM input pin at high, which then turns the LED 330 on. The second interrupt is responsive to the falling edge and turns the LED 330 off. Further, the microcontroller 400 is preferably programmed to turn on the LED 330 on every second camera signal. This enables the camera to take alternately one image with LED excitation light and one image with no LED excitation light, which is important for the cancellation of noise caused by ambient light.

The controller 140 in FIGS. 1, 2 and 4 above, as well as FIG. 9, discussed below, preferably includes control and image analysis software. This control and image analysis software can be suitably implemented with the LabVIEW programming platform (LabVIEW 2010+Vision module) sold by National Instruments.

Figure 6:
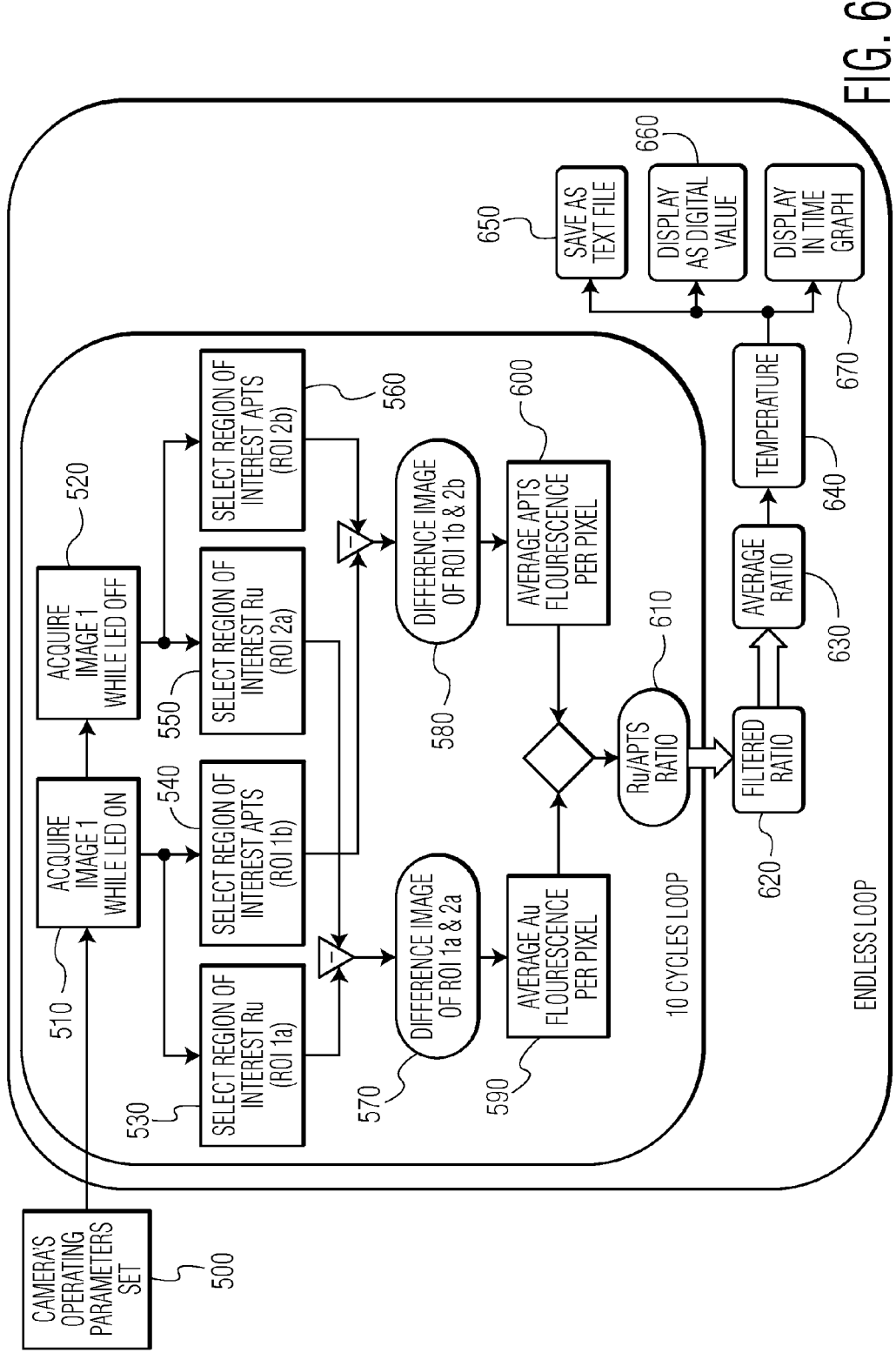
FIG. 6 is a flowchart showing preferred key functional steps executed by the controller 140 for a scenario where the Ruphen containing hydrogel and APTS containing hydrogel that make up the luminescence-based gel sensor are positioned adjacent to each other or otherwise spatially separated from each other, such their emission signals are spatially separated when they reach the detector.

FIG. 6 shows the preferred key functional steps of the control and image analysis software for the scenario where the Ruphen containing hydrogel and APTS containing hydrogel that make up the luminescence-based gel sensor 110 are positioned adjacent to each other or otherwise spatially separated from each other, such their emission signals are spatially separated when they reach the CCD camera 350. The process starts at step 500, where the CCD camera 350 is set at continuous acquisition mode (typically 30 frames per second), the CCD camera 350 exposure time is preferably set to 16 ms and the CCD camera 350 resolution is preferably set at 640×480.

At steps 510 and 520, two sequential image frames are acquired from the CCD camera 350. As discussed above, the LED controller 340 ensures the first image frame is with the LED 330 off and the second image frame is with the LED 330 on. In this way, the first image frame corresponds to the intensity of the ambient light only, while second image frame corresponds to the intensity of the ambient light plus the fluorescence from the luminescence-based gel sensor 110.

At steps 530 and 540, the process identifies the regions in the first image frame that correspond to the Ruphen emission (ROI 1*a*) and the APTS emission (ROI 1*b*), respectively. At steps 550 and 560, the process identifies the regions in the second image frame that correspond to the Ruphen emission (ROI 2*a*) and the APTS emission (ROI 2*b*), respectively.

At step 570, pixel values for ROI 1*a* are subtracted from pixel values for ROI 2*a*. At step 580, pixel values for ROI 1*b* are subtracted from pixel values for ROI 2*b*. This effectively reduces or eliminates the contribution of ambient light to the pixel values, such that only the contribution from the Ruphen and APTS fluorescence emission remain.

Then, at steps 590 and 600 the average Ruphen fluorescence and APTS fluorescence per pixel, respectively, is calculated. This is suitably done by extracting the images of the Ruphen and APTS fluorescent gels, and then manually setting the spatial coordinates of the Ruphen and APTS fluorescent gel images.

At step 610, the ratio of the average Ruphen fluorescence per pixel to the average APTS fluorescence per pixel is calculated. At step 620, the ratio is preferably subjected to a 90 point moving average filter, which minimizes possible influence of rapid changes in illumination (e.g., people walking close the luminescence-based gel sensor 110). This moving average filtering yields an average ratio 630.

This average ratio is then linearly scaled to temperature at step 640. The temperature value can then be saved as a text file (step 650), displayed as a digital value on a digital display (step 660) and/or displayed as a time graph (step 670). The user has the option to change various parameters including, but not limited to, the exposure time of the CCD camera 350 (frame rate), the resolution of the CCD camera 350, the parameters of the digital filtering step 620.

Figure 7B:
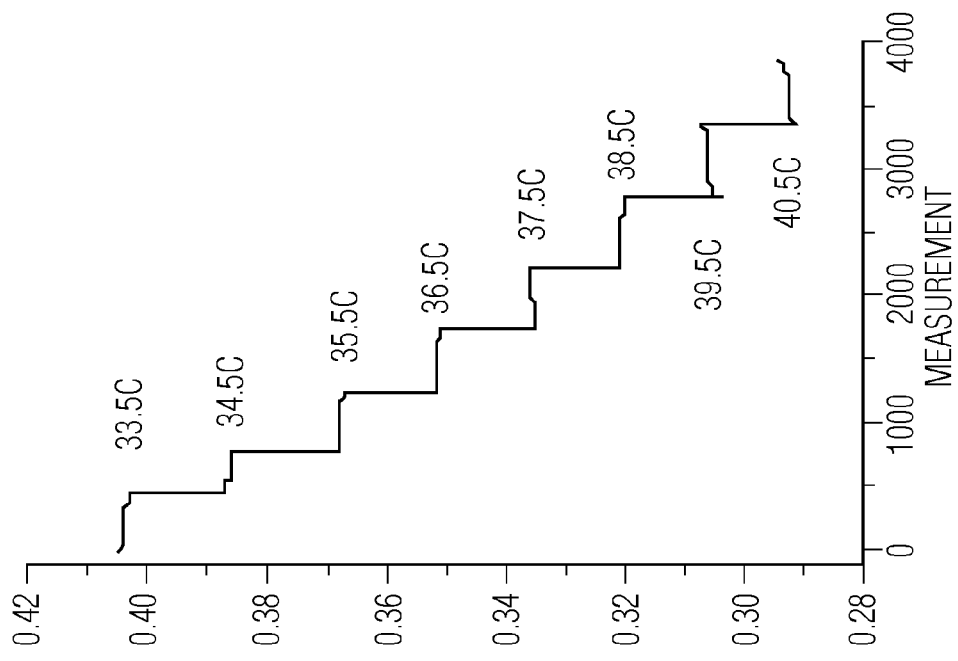
FIG. 7 are plots showing the ratio of fluorescence intensity of Ruphen to APTS as a function of temperature.
Figure 7A:
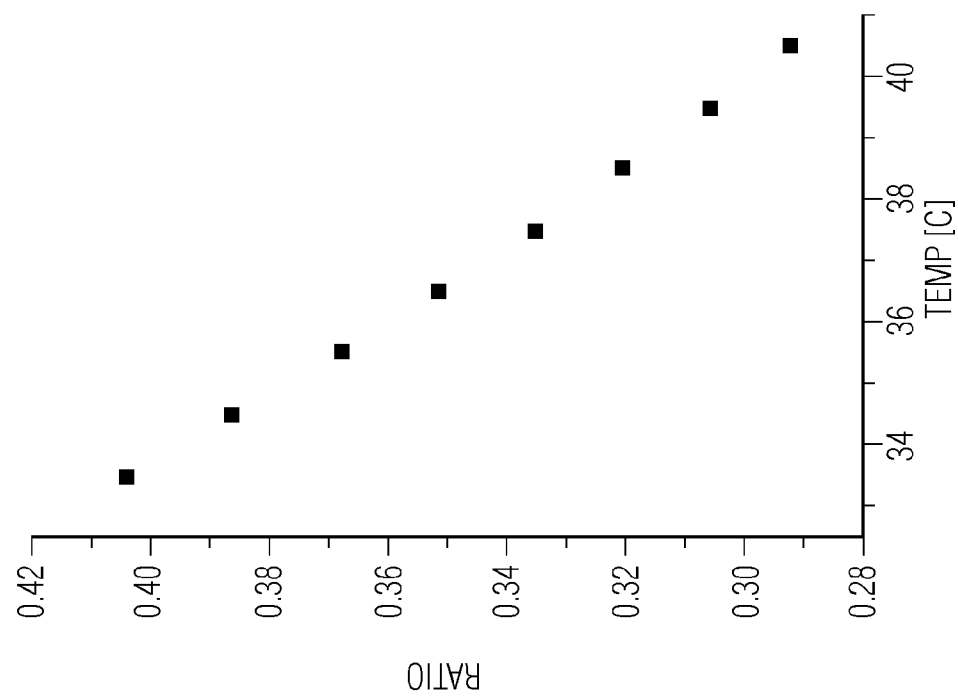

The system 300 of FIG. 4 was used to determine the effect of temperature changes on the luminescence-based gel sensor 110. As shown in FIG. 7, within a physiologically relevant temperature range, the ratio of the fluorescence intensity of Ruphen and APTS correlates linearly to the temperature of the thermal block 310. Based on this data, the luminescence-based gel sensor 110 has a resolution of 0.0032° C.

Figure 8:
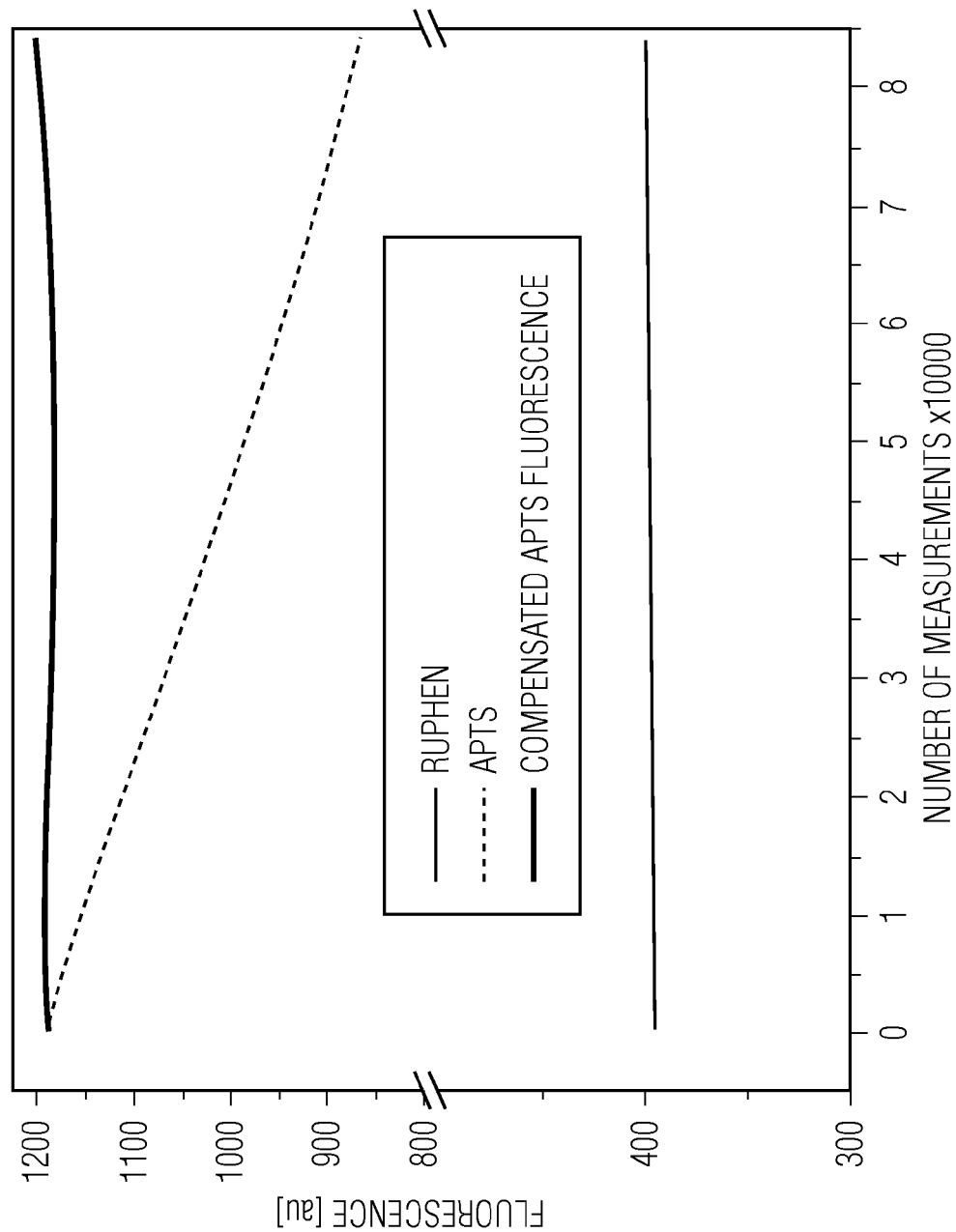
FIG. 8 is a plot showing the decrease in fluorescence of Ruphen and APTS due to bleaching effects.

Photobleaching is an intrinsic property of the luminophores and is influenced by the presence of oxidants, such as oxygen. Since the luminescence-based gel sensor 110 employs two different luminophores, their bleaching rates will differ from one another. As shown in FIG. 8, the fluorescence of APTS drops almost linearly by 25% from its original value after 8 hours of illumination, while the fluorescence of Ruphen remains virtually unchanged. This divergence could lead to a significant drift of the measurement signal if no compensation measures are undertaken. To correct this discrepancy, a compensation loop is preferably implemented in the control and image analysis software. The compensation algorithm takes into consideration the exposure time of the luminophore to the blue LED excitation light and compensates for the drop of the APTS fluorescence. It is also assumed that the ambient oxygen concentrations are constant within the duration of the measurements. As can be seen in FIG. 8, the software compensated for the decrease in fluorescence of APTS over an 8-hour period to a satisfactory extent. The average compensated value is 1189.9 and its standard deviation is ±4.21.

Figure 9:
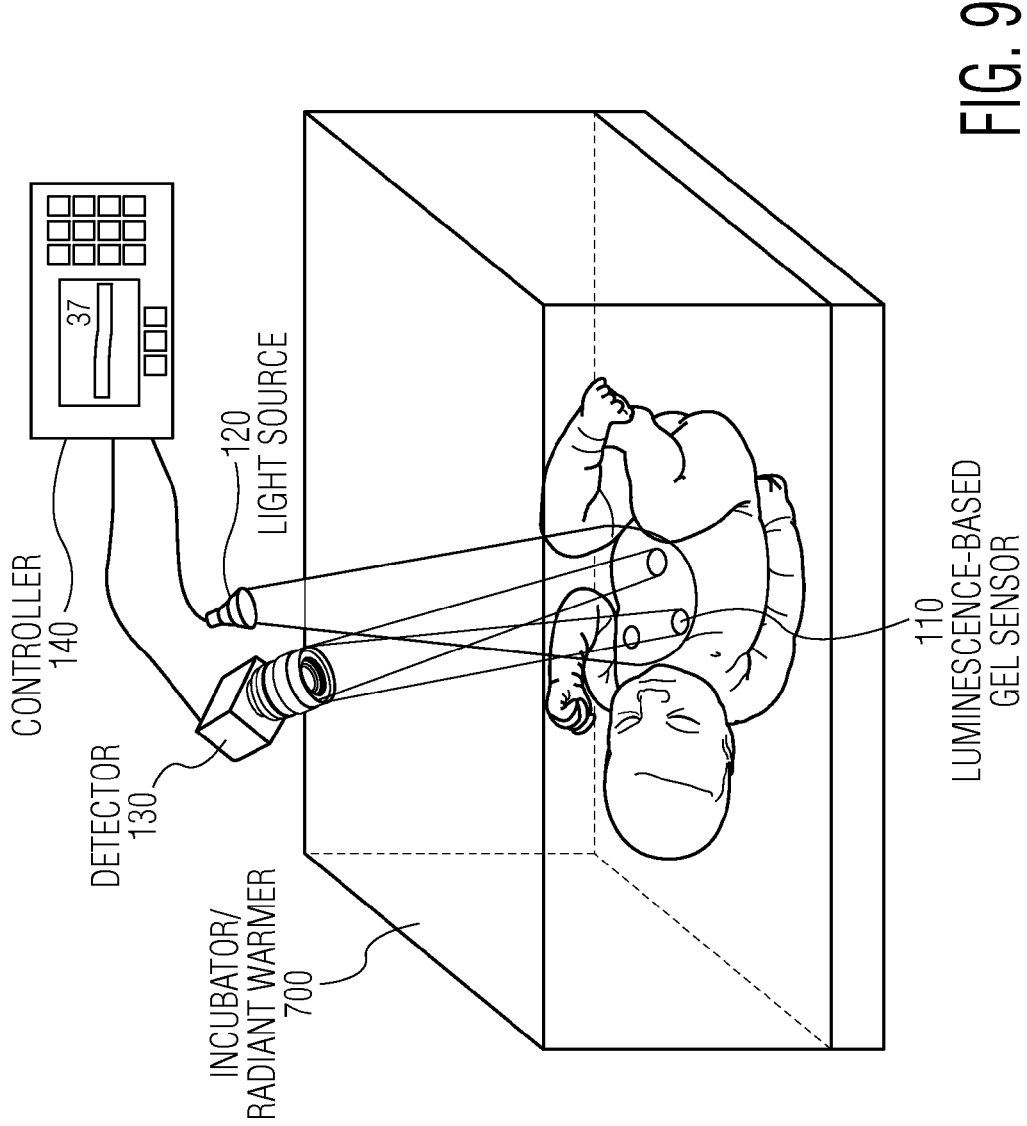
FIG. 9 is a schematic diagram of an incubator/radiant warmer that incorporates a remote body temperature sensing system, in accordance with an embodiment of the present invention.

The luminescence-based gel sensor 110 of the present invention is particularly suitable as a remote body temperature sensing system in incubators and radiant warmers 700 for infant and neonatal care, as shown in FIG. 9. Temperature measurements can be taken remotely without the need for the standard adhesive thermistors that can irritate or damage the baby's skin. The luminescence-based gel sensors 110 are easy to apply and remove without the risk of damaging the baby's skin. Further, the luminescence-based gel sensors 110 do not require a wired connection, thereby eliminating the risk of the baby getting tangled in wires. In addition, because the remote body temperature system can operate in the visible spectrum, there is no detector interference from the radiant warmers used in incubators and radiant warmers.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. For example, although the luminescence-based gel sensors have been described in connection with a remote body temperature sensing system, it can be adapted for the remote sensing of other parameters by choosing the appropriate light sources and luminescence-based gel sensors.

What is claimed is:

1. A noninvasive remote sensor for measuring temperature, comprising:
   at least a first gel;
   a first type of fluorophore embedded in at least the first gel, wherein the first type of fluorophore emits first emission light via luminescence in response to first excitation light, wherein the luminescence of the first type of fluorophore varies as a function of temperature;
   a second type of fluorophore embedded in at least the first gel that also contains the first type of fluorophore, wherein the second type of fluorophore emits second emission light via luminescence in response to second excitation light, wherein the luminescence of the second type of fluorophore varies as a function of temperature;
   a light detector positioned to detect the first and second emission light, wherein the light detector generates at least one detector signal corresponding to the first and second emission light, wherein at least one characteristic of the at least one detector signal represents both at least one parameter of the first emission light of the first emission light and at least one parameter of the first emission light; and
   a process controller in communication with the light detector, wherein the process controller determines a temperature value of an object in contact with at least the first gel based on the at least one characteristic of the at least one detector signal, wherein the temperature value is dependent on the at least one characteristic of the at least one detector signal such that a change in the at least one characteristic of the at least one detector signal will result in a change in the determined temperature value.

2. The sensor of claim 1, wherein the at least one characteristic comprises a ratio F1/F2, where F1 corresponds to an intensity of light emitted from the first type of fluorophore and F2 corresponds to an intensity of light emitted from the second type of fluorophore.

3. The sensor of claim 1, wherein the at least one characteristic corresponds to a decay time difference between the first and second emission light when the first and second excitation light is intensity modulated.

4. The sensor of claim 1, wherein the first and second types of fluorophores comprise fluorophores that are excitable by visible light.

5. The sensor of claim 4, wherein the first type of fluorophore comprises ruthenium(II) tris(1, 10-phenanthroline).

6. The sensor of claim 4, wherein the second type of fluorophore comprises 8-aminopyrene-1,3,6-trisulfonic acid.

7. The sensor of claim 1, wherein at least the first gel is non-toxic and hypoallergenic.

8. The sensor of claim 1, wherein at least the first gel has anti-bacterial properties.

9. The sensor of claim 1, wherein at least the first gel comprises a hydrogel matrix.

10. The sensor of claim 9, wherein at least the first gel comprises chitosan or glyceryl polyacrylate.

11. The sensor of claim 3, wherein the light detector comprises a CCD camera.

12. The sensor of claim 11, wherein the process controller utilizes lock-in imaging to measure the decay time difference.

13. A noninvasive remote sensor for measuring temperature, comprising:
 a first;
 a first type of fluorophore embedded in the first hydrogel, wherein the first type of fluorophore emits first emission light via luminescence in response to first excitation light, wherein the luminescence of the hydrogel first type of fluorophore varies as a function of temperature;
 a second hydrogel;
 a second type of fluorophore embedded in the second hydrogel, wherein the second type of fluorophore emits second emission light via luminescence in response to second excitation light, wherein the luminescence of the second type of fluorophore varies as a function of temperature;
 at least one light detector positioned to detect the first and second emission light, wherein the light detector generates at least one detector signal corresponding to the first and second emission light, wherein at least one characteristic of the at least one detector signal represents both at least one parameter of the first emission light and at least one parameter of the second emission light; and
 a process controller in communication with the at least one light detector, wherein the process controller determines a temperature value of an object in contact with both the first and second hydrogels based on the at least one characteristic of the at least one detector signal, wherein the determined temperature value is dependent on the at least one characteristic of the at least one detector signal such that a change in the at least one characteristic of the at least one detector signal will result in a change in the determined temperature value.

14. The sensor of claim 13, wherein the at least one characteristic comprises a ratio F1/F2, where F1 corresponds to an intensity of light emitted from the first type of fluorophore and F2 corresponds to an intensity of light emitted from the second type of fluorophore.

15. The sensor of claim 13, wherein the first and second types of fluorophores comprise fluorophores that are excitable by visible light.

16. The sensor of claim 15, wherein the first type of fluorophore comprises ruthenium(II) tris(1, 10-phenanthroline).

17. The sensor of claim 15, wherein the second type of fluorophore comprises 8-aminopyrene-1,3,6-trisulfonic acid.

18. The sensor of claim 13, wherein the first and second hydrogels each comprise chitosan or glyceryl polyacrylate.

* * * * *